(12) United States Patent
Ku et al.

(10) Patent No.: US 11,565,030 B2
(45) Date of Patent: Jan. 31, 2023

(54) BLOOD PRESSURE PREDICTION METHOD AND ELECTRONIC DEVICE USING THE SAME

(71) Applicant: Wistron Corporation, New Taipei (TW)

(72) Inventors: Che-Wen Ku, New Taipei (TW); Chih-Yi Chien, New Taipei (TW)

(73) Assignee: Wistron Corporation, New Taipei (TW)

( * ) Notice: Subject to any disclaimer, the term of this patent is extended or adjusted under 35 U.S.C. 154(b) by 782 days.

(21) Appl. No.: 16/561,031

(22) Filed: Sep. 5, 2019

(65) Prior Publication Data

US 2020/0397972 A1 Dec. 24, 2020

(30) Foreign Application Priority Data

Jun. 20, 2019 (TW) ................................ 108121585

(51) Int. Cl.
*A61M 1/36* (2006.01)
*A61M 1/34* (2006.01)
(Continued)

(52) U.S. Cl.
CPC ............ *A61M 1/3639* (2013.01); *A61B 5/021* (2013.01); *A61B 5/4836* (2013.01); *A61B 5/72* (2013.01);
(Continued)

(58) Field of Classification Search
CPC .............. A61M 1/1603; A61M 1/1605; A61M 1/1613; A61M 1/3413; A61M 1/3663; A61M 1/3639; A61M 2205/18; A61M 2205/3368; A61M 2205/50; A61M 2230/30; A61B 5/021; A61B 5/4836;
(Continued)

(56) References Cited

U.S. PATENT DOCUMENTS

2019/0217002 A1 7/2019 Urakabe

FOREIGN PATENT DOCUMENTS

| CA | 3035955 A1 * | 3/2018 |
|---|---|---|
| CN | 109803694 | 5/2019 |

OTHER PUBLICATIONS

"Office Action of Taiwan Counterpart Application", dated May 18, 2020, p. 1-p. 12.

* cited by examiner

*Primary Examiner* — John Kim
(74) *Attorney, Agent, or Firm* — JCIPRNET

(57) ABSTRACT

A blood pressure prediction method and an electronic device using the same are provided. The method includes the following steps. A training data set is collected. A first blood pressure prediction model is established according to the training data set. Hemodialysis parameter data of a target patient is received, wherein the hemodialysis parameter data includes a first hemodialysis parameter at a previous time point and a second hemodialysis parameter at a current time point. A hemodialysis parameter variation amount between the first hemodialysis parameter and the second hemodialysis parameter is calculated. The hemodialysis parameter variation amount is provided to the first blood pressure prediction model to generate a prediction blood pressure variation associated with a next time point. An operation is performed according to the prediction blood pressure variation of the target patient.

18 Claims, 7 Drawing Sheets

(51) Int. Cl.
   *A61M 1/16* (2006.01)
   *A61B 5/021* (2006.01)
   *G16H 50/20* (2018.01)
   *G16H 50/50* (2018.01)
   *G16H 50/70* (2018.01)
   *G16H 20/40* (2018.01)
   *A61B 5/00* (2006.01)
   *G16H 20/17* (2018.01)

(52) U.S. Cl.
   CPC .......... *A61B 5/7264* (2013.01); *A61B 5/7275* (2013.01); *A61M 1/1603* (2014.02); *A61M 1/1605* (2014.02); *A61M 1/1613* (2014.02); *A61M 1/3413* (2013.01); *A61M 1/3663* (2013.01); *G16H 20/17* (2018.01); *G16H 20/40* (2018.01); *G16H 50/20* (2018.01); *G16H 50/50* (2018.01); *G16H 50/70* (2018.01); *A61M 2205/18* (2013.01); *A61M 2205/3368* (2013.01); *A61M 2205/50* (2013.01); *A61M 2230/30* (2013.01)

(58) Field of Classification Search
   CPC ....... A61B 5/72; A61B 5/7264; A61B 5/7275; G16H 20/17; G16H 20/40; G16H 50/20; G16H 50/50; G16H 50/70
   See application file for complete search history.

BLOOD PRESSURE PREDICTION METHOD AND ELECTRONIC DEVICE USING THE SAME

CROSS-REFERENCE TO RELATED APPLICATION

This application claims the priority benefit of Taiwan application serial no. 108121585, filed on Jun. 20, 2019. The entirety of the above-mentioned patent application is hereby incorporated by reference herein and made a part of this specification.

BACKGROUND

Technical Field

The disclosure is directed to a physiological state prediction method and more particularly, to a blood pressure prediction method and an electronic device using the same.

Description of Related Art

Hemodialysis (also referred to as kidney dialysis) is one of common medical treatments. During a process of hemodialysis, the blood is drained to a dialysis apparatus (also referred to as a kidney dialysis machine) and then returned to the body. Specifically, the blood is first drained out of the body, then urinary toxin and moisture is removed from the blood by means of diffusion and an ultrafiltration of a semi-permeable membrane, and the blood is lastly guided back to the body. Generally, after a medical personnel completes setting each hemodialysis parameter of the dialysis apparatus, a patient may start a hemodialysis treatment via the dialysis apparatus.

It should be noted that unstable blood pressure is one of the common problems that a patient who needs the hemodialysis may encounter. The medical personnel may usually feel troublesome about the uncontrollable hypertension and hypotension in the hemodialysis, while the patient may also thus experience various kinds of discomfort. When the hypotension occurs during the period of hemodialysis, the hemodialysis treatment is forced to end early or interrupt, and after a long term, it would consequently result in a phenomenon of insufficient removal of urea toxin and even cause the increase in the mortality of the patient. Thus, during the process of hemodialysis, the medical personnel usually has to rely on his/her experience and historic dialysis data of the patient to set hemodialysis parameters of the dialysis apparatus, expecting to stabilize the patient's blood pressure and mitigate the occurrence of the hypotension in the hemodialysis. However, not to mention that an inexperienced medical personnel is unable to immediately predict the occurrence of the hypotension in the hemodialysis, even for an experienced medical personnel, the physical condition of each patient is considerably different, and thus, how to adaptively adjust the hemodialysis parameters of the dialysis apparatus to prevent the hypotension in the hemodialysis is indeed a great challenge.

SUMMARY

Accordingly, the disclosure provides a blood pressure prediction method and an electronic device using the same, capable of estimating a situation of blood pressure drop in advance for patient during a dialysis process.

According to an embodiment of the disclosure, a blood pressure prediction method including the following steps in provided. A training data set is collected. A first blood pressure prediction model is established according to the training data set. Hemodialysis parameter data of a target patient is received, wherein the hemodialysis parameter data includes a first hemodialysis parameter at a previous time point and a second hemodialysis parameter at a current time point. A hemodialysis parameter variation amount between the first hemodialysis parameter and the second hemodialysis parameter is calculated. The hemodialysis parameter variation amount is provided to the first blood pressure prediction model to generate a prediction blood pressure variation associated with a next time point. An operation is performed according to the prediction blood pressure variation of the target patient.

According to an embodiment of the disclosure, an electronic device is provided, which includes a storage circuit storing a plurality of modules and a processor. The processor is configured to access the modules to collect a training data set; establish a first blood pressure prediction model according to the training data set; receive hemodialysis parameter data of a target patient, wherein the hemodialysis parameter data includes a first hemodialysis parameter at a previous time point and a second hemodialysis parameter at a current time point; calculate a hemodialysis parameter variation amount between the first hemodialysis parameter and the second hemodialysis parameter; provide the hemodialysis parameter variation amount to the first blood pressure prediction model to generate a prediction blood pressure variation associated with a next time point; and perform an operation according to the prediction blood pressure variation of the target patient.

Based on the above, in the embodiments of the disclosure, the hemodialysis parameter variation amount in the hemodialysis can be instantly provided to the blood pressure prediction model, so as to predict the prediction blood pressure variation associated with the next time point. Thereby, the medical personnel can be assisted to predict the occurrence of hypotension in the hemodialysis in advance, such that the medical personnel can timely conduct appropriate treatments. Moreover, in comparison with directly predicting a blood pressure value of a patient at a specific time, the embodiments of the disclosure can contribute to enhancing prediction accuracy of the prediction blood pressure variation by using more information, so as to ensure the stability of the blood pressure of the patient under hemodialysis.

To make the above features and advantages of the disclosure more comprehensible, embodiments accompanied with drawings are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

Part of the embodiments of the disclosure will be described in detail with reference to the accompanying drawings below, and regarding the element symbols used in the description below, the same or similar element symbols appearing in different accompanying drawings are considered as the same or similar elements. These embodiments are only part of the disclosure and do not disclose all the implementable manners of the disclosure. More precisely, these embodiments are only examples of the method and device within the scope of the claims of the disclosure.

Figure 1:
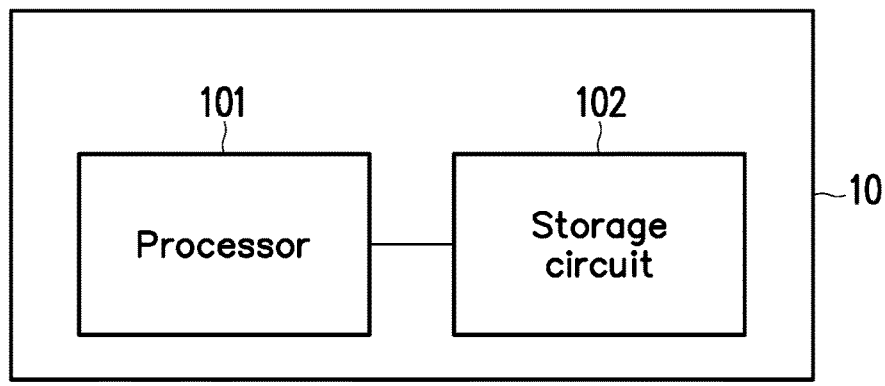
FIG. 1 is a block diagram illustrating an electronic device according to an embodiment of the disclosure.

FIG. 1 is a block diagram illustrating an electronic device according to an embodiment of the disclosure. However, it is illustrated only for descriptive convenience, but construes no limitations to the disclosure. Referring to FIG. 1, an electronic device 10 is configured to predict a blood pressure variation of a patient during a hematotherapy of the patient. The electronic apparatus 10 includes a processor 101 and a storage circuit 102.

The storage circuit 102 is configured to store data, software modules and program codes, which may be any type of fixed or movable random access memory (RAM), read only memory (ROM), a flash memory, a hard disk or other similar devices, integrated circuits and a combination thereof.

The processor 101 is configured to perform a blood pressure prediction method provided herein, which may be a central processing unit (CPU), a graphics processing unit (GPU) or any other programmable microprocessor for general or special use, a digital signal processor (DSP), a programmable controller, an application specific integrated circuit (ASIC), a programmable logic device (PLD) or other similar devices, chips, integrated circuits or a combination thereof. In the embodiments of the disclosure, the processor 101 may load the program codes or modules recorded in the storage circuit 102 to perform the blood pressure prediction method provided by the embodiments of the disclosure.

In the embodiments of the disclosure, the electronic device 10 may be a medical apparatus, a personal computer, a notebook computer, a workstation, a server, a smart device with a computation function or a combination of the aforementioned devices, and the type of the electronic device 10 is not limited in the disclosure.

Figure 2:
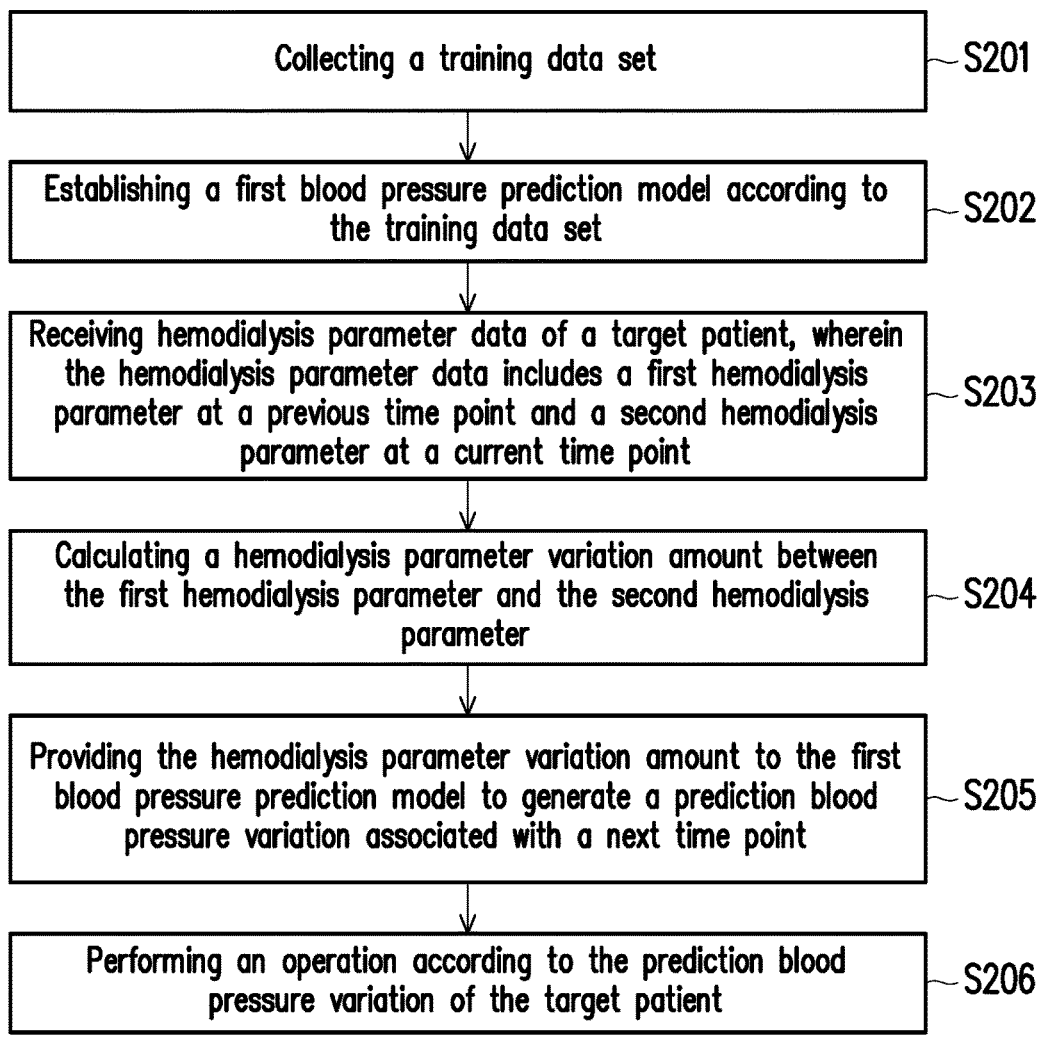
FIG. 2 is a flowchart illustrating a blood pressure prediction method according to an embodiment of the disclosure.

FIG. 2 is a flowchart illustrating a blood pressure prediction method according to an embodiment of the disclosure. Referring to FIG. 1 and FIG. 2, the method of the present embodiment is applicable to the electronic device 10 of the previous embodiment, and detailed steps of the blood pressure prediction method of the present embodiment will be described below with reference to each element of the electronic device 10.

In step S201, the processor 101 collects a training data set. Specifically, the training data set may include data of a plurality of patients when conducting hemodialysis every time in the past, such as physiological data, medical record data, climate data, hemodialysis therapy data, etc. Among them, the hemodialysis therapy data of the patients when conducting the hemodialysis every time in the past may include hemodialysis parameter data of the dialysis apparatus and blood pressure data during the period of hemodialysis. The data in the training data set may be obtained from the dialysis apparatus or returned from other medical apparatuses. Further, alternatively, the data in the training data set may be provided by a medical information system of a medical institution. Moreover, alternatively, the data in the training data set may be provided by an external database (e.g., a database of a climate center).

In step S202, the processor 101 establishes a first blood pressure prediction model according to the training data set. The first blood pressure prediction model refers to a rule established by the processor 101 performing machine learning according to the training data set and configured to predict a blood pressure variation. In the embodiments of the disclosure, the processor 101 may establish the first blood pressure prediction model according to a supervised machine learning algorithm. The first blood pressure prediction model after being established may be recorded in the storage circuit 102, so as to be used to predict a trend of the blood pressure variation for a patient during a period that the patient conducts a hemodialysis. The supervised machine learning algorithm may include a regression analysis algorithm, an eXtreme gradient boosting (XGboost) algorithm, a bootstrap aggregating (Bagged) algorithm, a neural network algorithm, a random forest algorithm, an elastic net algorithm, a least absolute shrinkage and selection operator (LASSO) algorithm, a k-nearest neighbor classification (KNN) algorithm, a support vector regression algorithm or an ensemble learning algorithm and so on, which is not limited in the disclosure.

During a period that a target patient conducts a hemodialysis, in step S203, the processor 101 receives hemodialysis parameter data of the target patient, wherein the hemodialysis parameter data includes a first hemodialysis parameter at a previous time point and a second hemodialysis parameter at a current time point. Specifically, a dialysis apparatus may continuously report current hemodialysis parameters to the processor 101 through a gateway. In an embodiment of the disclosure, the dialysis apparatus may periodically report the hemodialysis parameters. Alternatively, the dialysis apparatus may report the hemodialysis parameters in response to an adjustment of the hemodialysis parameters by a medical personnel. Thus, the processor 101 may receive the hemodialysis parameters corresponding to different time points. In the embodiments of the disclosure, each of the first hemodialysis parameter and the second hemodialysis parameter may include one or a combination of an ultrafiltration rate, a dialysate concentration, a dialysate temperature or a blood flow rate. For instance, the processor 101 may receive an ultrafiltration rate corresponding to a previous time point of 11:00 and an ultrafiltration rate corresponding to a current time point of 11:30.

In step S204, the processor 101 calculates a hemodialysis parameter variation amount between the first hemodialysis parameter and the second hemodialysis parameter. In step S205, the processor 101 provides the hemodialysis parameter variation amount to the first blood pressure prediction model to generate a prediction blood pressure variation associated with a next time point. To be detailed, in an embodiment of the disclosure, the first blood pressure prediction model serves the hemodialysis parameter variation amount as a model input parameter, thereby predicting the prediction blood pressure variation at the next time point. It should be mentioned that if the hemodialysis parameters are not adjusted or changed, the hemodialysis parameter variation amount is 0. For instance, the processor 101 may obtain a hemodialysis parameter variation amount between a blood flow rate at a previous time point and a blood flow rate at a current time point, and input the hemodialysis parameter variation amount related to the blood flow rate to the first blood pressure prediction model to predict the prediction blood pressure variation associated with the next time point. Because the dialysis apparatus may report the hemodialysis parameters to the processor 101 periodically or in response to the adjustment of the hemodialysis parameters by the medical personnel, the processor 101 may predict the prediction blood pressure variation in the future periodically or in response to the adjustment of the hemodialysis parameters by the medical personnel.

It may be correspondingly known that in the embodiments of the disclosure, after the processor 101 collects the training data set of the plurality of patients, the processor 101 may serve a blood pressure variation during the period that each patient conducts the hemodialysis in the past as an expectation output in the supervised machine learning algorithm and serve the hemodialysis parameter variation amount during the period that each patient conducts the hemodialysis in the past as an input object in the supervised machine learning algorithm, thereby training the blood pressure prediction model of the prediction blood pressure variation.

Figure 3A:
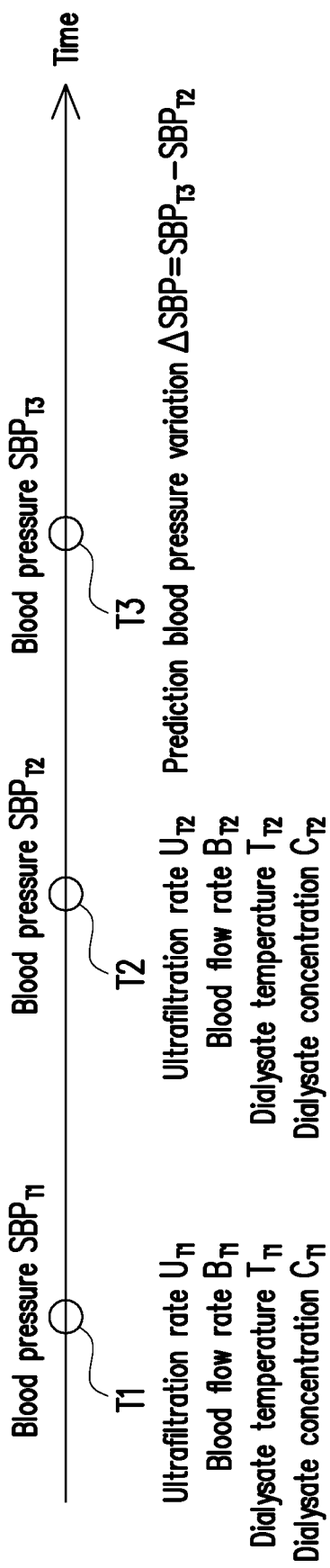
FIG. 3A is a schematic diagram illustrating training data analysis for establishing a blood pressure prediction model according to an embodiment of the disclosure.

For instance, referring to FIG. 3A, FIG. 3A is a schematic diagram illustrating training data analysis for establishing a blood pressure prediction model according to an embodiment of the disclosure. A training data set may include actual blood pressures $SBP_{T1}$, $SBP_{T2}$ and $SBP_{T3}$ of a specific patient which are measured respectively at time points T1, T2 and T3 during a period of hemodialysis. Moreover, the training data set may include actual hemodialysis parameters of the specific patient measured respectively at the time points T1, T2 and T3 during the period of hemodialysis. In this example, the actual hemodialysis parameter at the time point T1 includes an ultrafiltration rate $U_{T1}$, a blood flow rate $B_{T1}$, a dialysate temperature $T^{T1}$ and a dialysate concentration $C_{T1}$. The actual hemodialysis parameter at the time point T2 includes an ultrafiltration rate $U_{T2}$, a blood flow rate $B_{T2}$, a dialysate temperature $T_{T2}$ and a dialysate concentration $C_{T2}$. Therefore, the processor 101 may serve a hemodialysis parameter variation amount between the ultrafiltration rate $U_{T2}$ and the ultrafiltration rate $U_{T1}$, a hemodialysis parameter variation amount between the blood flow rate $B_{T2}$ and the blood flow rate $B_{T1}$, a hemodialysis parameter variation amount between the dialysate temperature $T_{T2}$ and the dialysate temperature $T_{T1}$ and a hemodialysis parameter variation amount between the dialysate concentration $C_{T2}$ and the dialysate concentration $C_{T1}$ as input objects in the supervised machine learning algorithm. Moreover, the processor 101 may serve an actual blood pressure variation ΔSBP between the blood pressure $SBP_{T2}$ and the blood pressure $SBP_{T3}$ (i.e., the blood pressure $SBP_{T3}$ is subtracted by the blood pressure $SBP_{T2}$) as an expectation output in the supervised machine learning algorithm. Accordingly, according to the supervised learning algorithm and the hemodialysis therapy data of the patients (including the actual blood pressures and the actual hemodialysis parameters corresponding to the different time points during the period of hemodialysis), the processor 101 may establish the first blood pressure prediction model configured to predict a prediction blood pressure variation at a future time point.

Figure 3B:
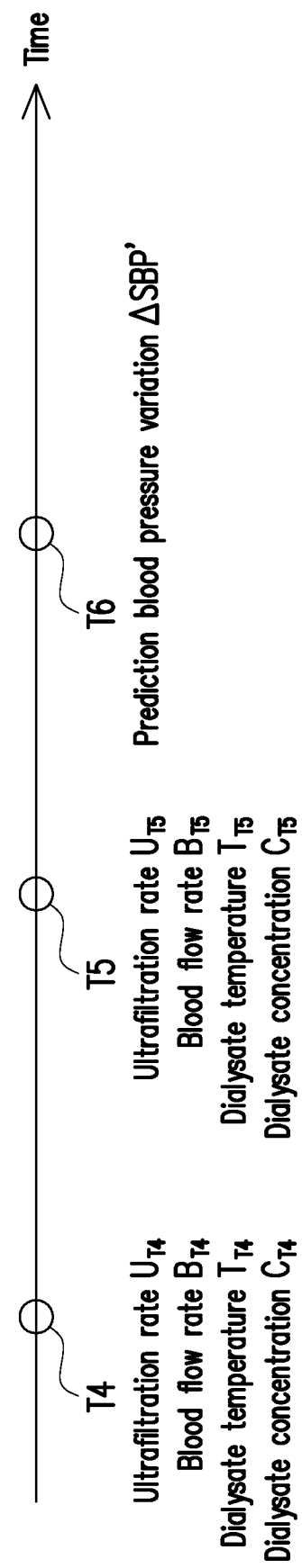
FIG. 3B is a schematic diagram illustrating prediction performed according to the blood pressure prediction model according to an embodiment of the disclosure.

Referring to FIG. 3B corresponding to FIG. 3A, FIG. 3B is a schematic diagram illustrating prediction performed according to the blood pressure prediction model according to an embodiment of the disclosure. During a period that a target patient conducts a hemodialysis, the dialysis apparatus may report a first hemodialysis parameter to the electronic device 10 at a previous time point T4, wherein the first hemodialysis parameter includes an ultrafiltration rate $U_{T4}$, a blood flow rate $B_{T4}$, a dialysate temperature $T_{T4}$ and a dialysate concentration $C_{T4}$. In addition, the dialysis apparatus may report a second hemodialysis parameter to the electronic device 10 at a current time point T5, wherein the second hemodialysis parameter includes an ultrafiltration rate $U_{T5}$, a blood flow rate $B_{T5}$, a dialysate temperature $T_{T5}$ and a dialysate concentration $C_{T5}$. Accordingly, the processor 101 may input a hemodialysis parameter variation amount between the ultrafiltration rate $U_{T4}$ and the ultrafiltration rate $U_{T5}$, a hemodialysis parameter variation amount between the blood flow rate $B_{T4}$ and the blood flow rate $B_{T5}$, a hemodialysis parameter variation amount between the dialysate temperature $T_{T4}$ and the dialysate temperature $T_{T5}$ and a hemodialysis parameter variation amount between the dialysate concentration $C_{T4}$ and the dialysate concentration $C_{T5}$ to the first blood pressure prediction model, such that the first blood pressure prediction model may generate a prediction blood pressure variation ΔSBP' associated with a next time point T6. In other words, at the current time point 15, the processor 101 is capable of predicting the prediction blood pressure variation ΔSBP' associated with the next time point T6 according to the first blood pressure prediction model.

Nevertheless, it should be mentioned that FIG. 3A and FIG. 3B serve the prediction of the prediction blood pressure variation at a future time point as an example. Nevertheless, the disclosure is not limited in this regard. In other embodiments, the processor 101 may predict a plurality of prediction blood pressure variations respectively corresponding to different future time points according to the hemodialysis parameter variation amount. Correspondingly, the first blood pressure prediction model may be trained by serving a plurality of actual blood pressures as expectation outputs based on a corresponding rule.

In step S206, the processor 101 performs an operation according to the prediction blood pressure variation of the target patient. In an embodiment, the processor 101 prompts the prediction blood pressure variation by means of icons or text on a display interface for the medical personnel's reference. Alternatively, in an embodiment, in response to the prediction blood pressure variation being greater than an alert threshold, the processor 101 may issue an alarm notification. Or, alternatively, in an embodiment, in response to the prediction blood pressure variation being greater than the alert threshold, the processor 101 may generate a suggestion hemodialysis parameter value according to the first blood pressure prediction model and the current hemodialysis therapy data, and prompt the suggestion hemodialysis parameter value to the medical personnel or control the hemodialysis apparatus to adjust the hemodialysis parameter according to the suggestion hemodialysis parameter value.

Moreover, in an embodiment of the disclosure, the medical personnel may input a test hemodialysis parameter to the electronic device 10, and the electronic device 10 may simulate a simulation blood pressure variation associated with the next time point based on the test hemodialysis parameter. Thereby, the medical personnel may input the test hemodialysis parameter into the electronic device 10 before actually adjusting the dialysis apparatus, so as to acquire whether the adjustment of the hemodialysis parameter is appropriate according to the simulation blood pressure variation.

Figure 4:
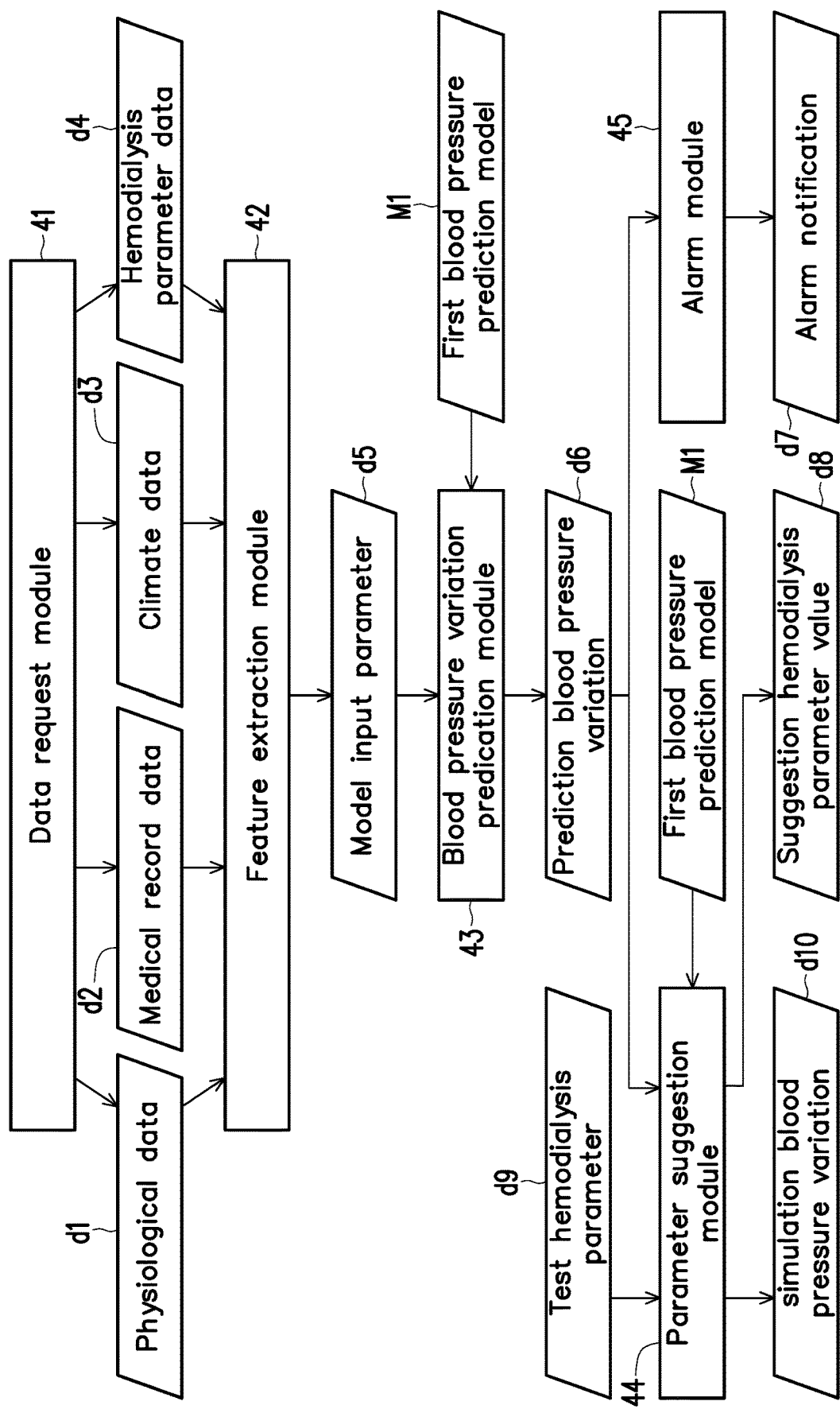
FIG. 4 is a schematic diagram illustrating a blood pressure prediction method according to an embodiment of the disclosure.

FIG. 4 is a schematic diagram illustrating a blood pressure prediction method according to an embodiment of the disclosure. In an example illustrated in FIG. 4, the prediction blood pressure variation during the period of hemodialysis is predicted by a data request module 41, a feature extraction module 42 and a blood pressure variation predication module 43, and a corresponding operation is performed by a parameter suggestion module 44 and an alarm module 45 according to the prediction blood pressure variation. The data request module 41, the feature extraction module 42, the blood pressure variation predication module 43, the parameter suggestion module 44 and the alarm module 45 may be obtained by implementing software elements recorded by the processor 101 and the storage circuit 102.

Referring to FIG. 4, after the target patient checks in at a medical institution or a kidney dialysis center, the data request module 41 may receive physiological data d1 and medical record data d2 of the target patient from a medical information system of the medical institution. The physiological data d1 obtained from the medical information system of the medical institution may include basic data of the target patient, such as gender, age, weight, height, etc. In addition, the physiological data d1 of the target patient may include the data obtained by measurement before after the hemodialysis, such as a blood pressure, a body temperature, etc. The medical record data d2 obtained from the medical information system of the medical institution may include data of the target patient, such as yeas of hemodialysis, a diabetes status, medical history, a medication situation, medical examination data (e.g., heme or other examination data) and so on. Moreover, the data request module 41 may receive climate data d3, such as weather, temperature, humidity, etc., from an external database. It should be noted that in the embodiments of the disclosure, the data request module 41 may obtain hemodialysis parameter data d4, which includes hemodialysis parameters belonging to different hemodialysis parameter types, from the dialysis apparatus.

Based on the rule of the first blood pressure prediction model M1, the feature extraction module 42 may calculate a model input parameter d5 required by a first blood pressure prediction model M1 according to the physiological data d1, the medical record data d2, the climate data d3 and the hemodialysis parameter data d4. It may be known based on the above that the model input parameter d5 required by the first blood pressure prediction model M1 at least includes a hemodialysis parameter variation amount generated according to the hemodialysis parameter data d4. It should be noted that in addition to the hemodialysis parameter variation amount, the model input parameter d5 required by the first blood pressure prediction model M1 may further include other data among the physiological data d1, the medical record data d2, the climate data d3, which is not limited in the disclosure. In other words, the blood pressure variation predication module 43 may provide the hemodialysis parameter variation amount, the physiological data d1, the medical record data d2 and the climate data d3 to the first blood pressure prediction model M1 to generate a prediction blood pressure variation d6 associated with the next time point.

Then, the blood pressure variation predication module 43 provides the model input parameter d5 to the first blood pressure prediction model M1 to generate the prediction blood pressure variation d6. In other words, the blood pressure variation predication module 43 may provide the physiological data d1, the medical record data d2, the climate data d3 and the hemodialysis parameter variation amount to the first blood pressure prediction model M1 to generate the prediction blood pressure variation d6 associated with the next time point.

In an embodiment of the disclosure, in response to the prediction blood pressure variation d6 associated with the next time point being greater than the alert threshold, the alarm module 45 issues an alarm notification d7. In the embodiments of the disclosure, a method of issuing the alarm notification includes, for example, emitting an alarm tone, displaying an alarm message, or sending an alarm message to a nursing station or an electronic device held by or a nursing personnel, but the disclosure is not limited thereto.

On the other hand, in an embodiment of the disclosure, in response to the prediction blood pressure variation d6 associated with the next time point being greater than the alert threshold, the parameter suggestion module 44 may generate a suggestion hemodialysis parameter value d8 through minimizing an output of the first blood pressure prediction model M1 according to the first blood pressure prediction model M1 and the hemodialysis parameter at the current time point (i.e., the second hemodialysis parameter). Specifically, when it is estimated according to the prediction blood pressure variation d6 that a phenomenon of an obvious blood pressure drop may likely occur to the target patient at the next time point, in a condition that the output of the first blood pressure prediction model M1 is minimized, the parameter suggestion module 44 may simulate an optimal suggestion hemodialysis parameter value d8 according to the hemodialysis parameter at the current time point. In other words, based on the prediction rule of the first blood pressure prediction model M1, if the dialysis apparatus is set according to the suggestion hemodialysis parameter value d8, the prediction blood pressure variation of the target patient in the future may be the minimum. Accordingly, the parameter suggestion module 44 may prompt the suggestion hemodialysis parameter value d8 to the medical personnel or set the dialysis apparatus according to the suggestion hemodialysis parameter value d8.

Moreover, in an embodiment of the disclosure, when the medical personnel want to know whether the adjustment of the hemodialysis parameter may effectively stabilize the blood pressure of the target patient, the parameter suggestion module 44 may receive a test hemodialysis parameter d9 input by the medical personnel. The parameter suggestion module 44 may provide the hemodialysis parameter variation amount between the actually configured hemodialysis parameter at the current time point (i.e., the second hemodialysis parameter) and the test hemodialysis parameter d9 to the first blood pressure prediction model M1 to generate a simulation blood pressure variation d10 associated with the next time point. In this way, by being prompted with the value of the simulation blood pressure variation d10, the medical personnel may acquire in advance whether the blood pressure of the target patient may keep stable during a subsequent process of hemodialysis, so as to determine whether to set the dialysis apparatus according to the test hemodialysis parameter d9.

Figure 5:
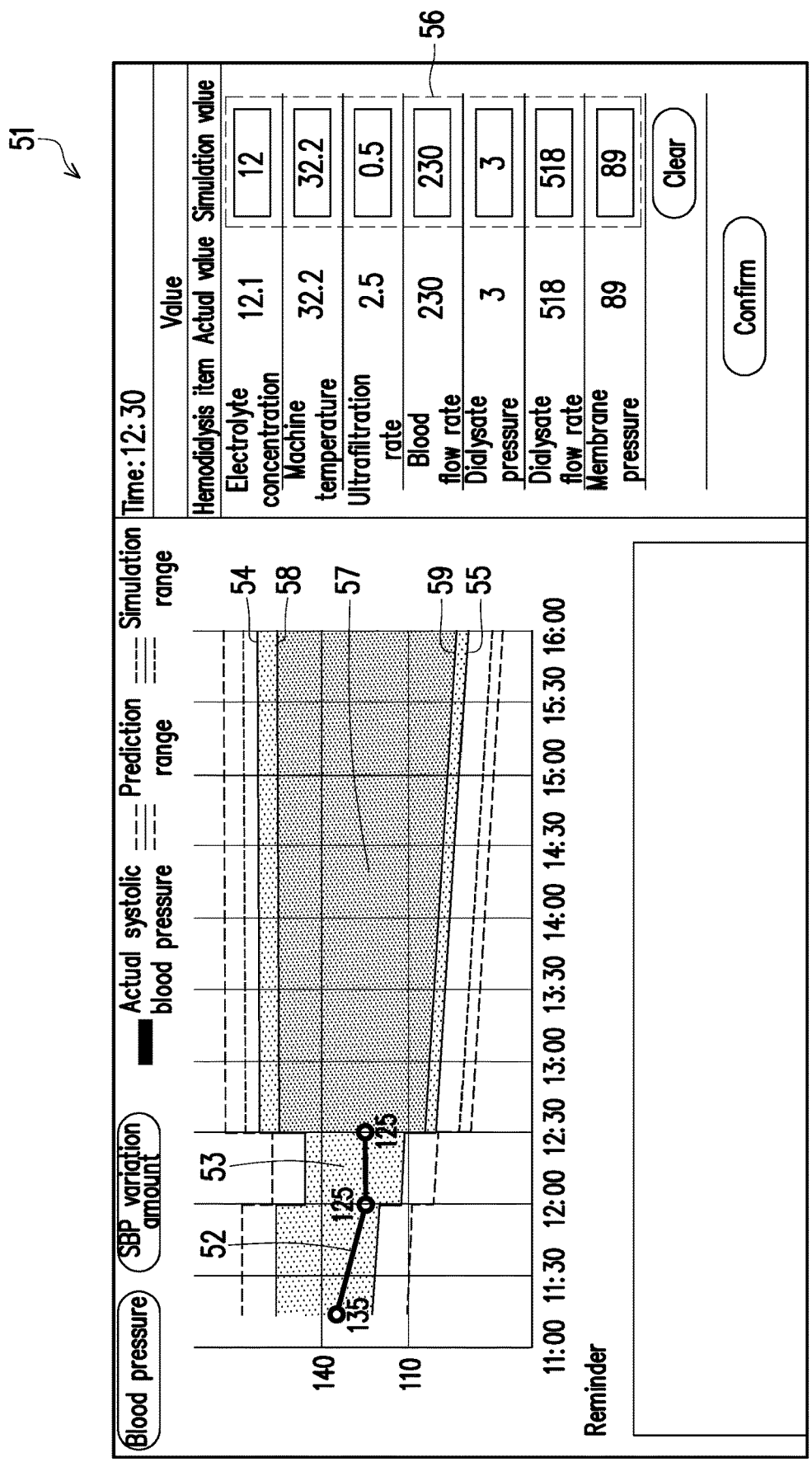
FIG. 5 is a schematic diagram illustrating a scenario of predicting a blood pressure variation according to an embodiment of the disclosure.

FIG. 5 is a schematic diagram illustrating a scenario of predicting a blood pressure variation according to an embodiment of the disclosure. Referring to FIG. 5 first, when the target patient conducts the hemodialysis, the electronic device 10 may control a display apparatus to provide a display interface 51. The display interface 51 displays an actual blood pressure value 52 of the target patient and a prediction blood pressure range 53 generated based on the prediction blood pressure variation. The prediction blood pressure range 53 is constituted by an upper limit 54 and a lower limit 55, and the upper limit 54 and the lower limit 55 may be obtained according to an actual blood pressure value of the target patient at a specific time point and at least one prediction blood pressure variation output by the first blood pressure prediction model. It is assumed that the current time point is 12:30, and through the display interface 51, the medical personnel may acquire a trend of the prediction blood pressure variation of the target patient in the future (i.e., a time after the current time point of 12:30) according to the prediction blood pressure range 53. Thereby, the medical personnel may further early determine whether the blood pressure of the target patient may keep stable in the subsequent process of hemodialysis through the display interface 51, so as to timely conduct appropriate treatments to prevent the occurrence of the hypotension in the hemodialysis.

Moreover, at the current time point of 12:30, the medical personnel may observe that the blood pressure of the target patient is likely to decrease gradually according to the prediction blood pressure range 53, and thus, the medical personnel may input the test hemodialysis parameter to a simulation value column 56. Based on the test hemodialysis parameter input by the medical personnel, the first blood pressure prediction model may generate at least one simulation blood pressure variation, and thus, the display interface 51 may display a simulation blood pressure range 57 generated based on the at least one simulation blood pressure variation. The simulation blood pressure range 57 is constituted by an upper limit 58 and a lower limit 59, and the upper limit 58 and the lower limit 59 may be obtained according to an actual blood pressure value of the target patient at a specific time point and the at least one simulation blood pressure variation output by the first blood pressure prediction model. Thereby, the medical personnel may know whether the test hemodialysis parameter in the simulation value column 56 may effectively stabilize the blood pressure of the target patient. In this way, the medical personnel may adjust the hemodialysis parameters of the dialysis apparatus not just according to his/her experience, thereby adaptively adjusting the hemodialysis parameters of the dialysis apparatus based on big data and the blood pressure prediction model established according to clinical data.

It is to be mentioned that in an embodiment of the disclosure, the aforementioned first blood pressure prediction model may be established according to the training data set of all patients, such that blood pressure variations of different target patients during the period of hemodialysis may be predicted based on the same first blood pressure prediction model. In another embodiment of the disclosure, the aforementioned first blood pressure prediction model may be established according to sub training data sets of a portion of the patients within a certain patient cluster. Thus, blood pressure variations during the period of hemodialysis may be predicted for different target patients based on different first blood pressure prediction models since different patients may be probably classified into different patient clusters.

Figure 6:
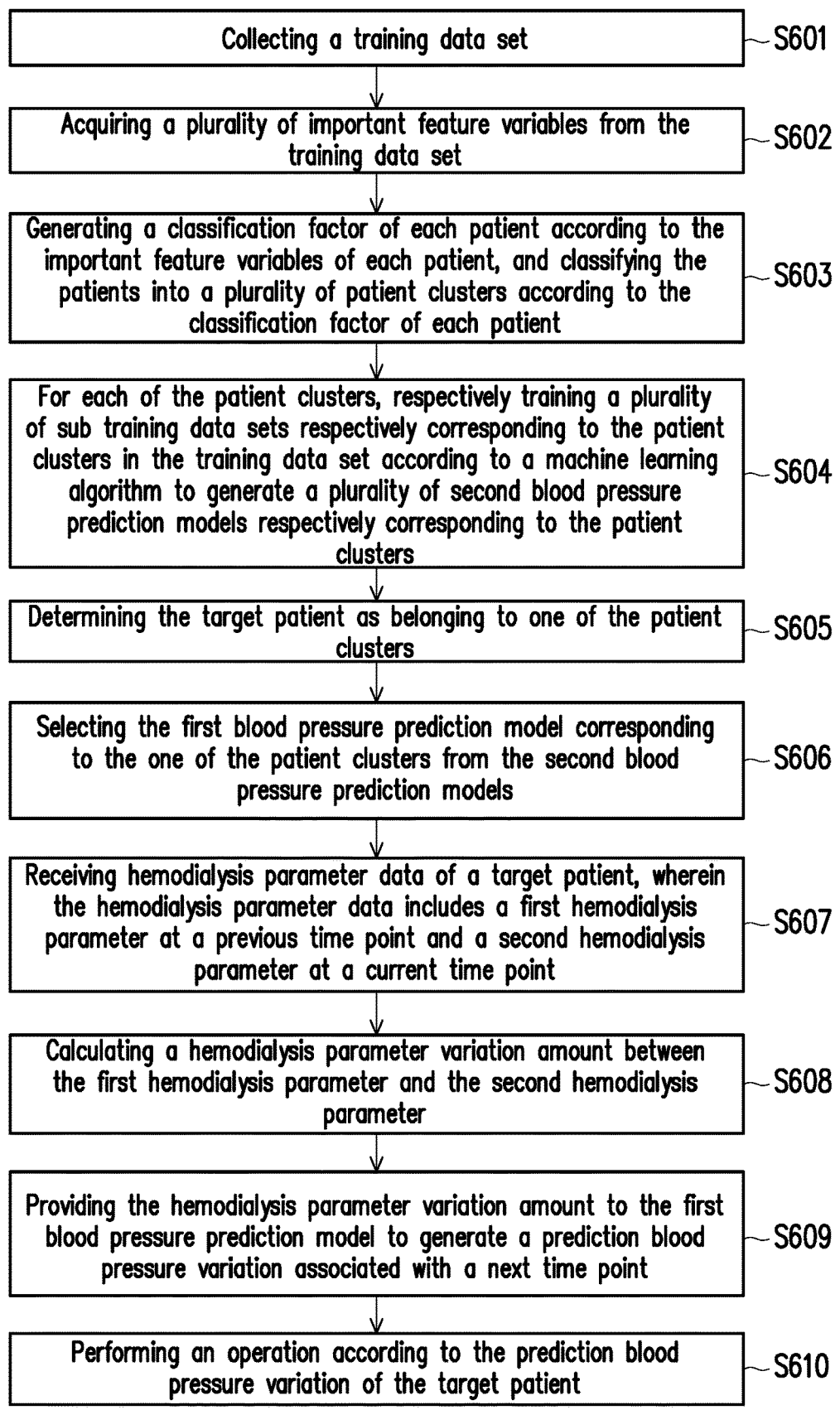
FIG. 6 is a flowchart illustrating a blood pressure prediction method according to an embodiment of the disclosure.

The implementation contents that the patients are first classified for establishing the blood pressure prediction models and conducting the blood pressure prediction will be further described below. FIG. 6 is a flowchart illustrating a blood pressure prediction method according to an embodiment of the disclosure. Referring to FIG. 1 and FIG. 6, the method of the present embodiment is applicable to the electronic device 10 of the previous embodiment, and detailed steps of the blood pressure prediction method of the present embodiment will be described with reference to each element of the electronic device 10.

In step S601, the processor 101 collects a training data set. The training data set may include various types of physiological data and hemodialysis therapy data used by a plurality of patients during the process of hemodialysis in the past. In step S602, the processor 101 acquires a plurality of important feature variables from the training data set. Specifically, the processor 101 may select a plurality of important feature variables according to a feature selection algorithm in feature engineering of machine learning, and these important feature variables may significantly influence the blood pressure variations. The feature selection algorithm includes, for example, regression model learning, random forest, chi-square test or decision tree, etc., which is not limited in the disclosure. For instance, the processor 101 may select a previous systolic blood pressure, an average of two previous blood pressures, a first systolic blood pressure, a previous total ultrafiltration amount, a previous diastolic blood pressure according to the feature selection algorithm to serve them as important feature variables for classifying the patients and predicting the prediction blood pressure variations.

In step S603, the processor 101 generates a classification factor of each patient according to the important feature variables of each patient and classifies the patients into a plurality of patient clusters according to the classification factor of each patient. In this case, in an embodiment of the disclosure, the processor 101 may perform statistical analysis on the important feature variables of each patient to generate the classification factor of each patient and classify each patient into one of the patient clusters by comparing the classification factor of each patient with at least one classification threshold. For instance, it is assumed that the important feature variables include first systolic blood pressures, the processor 101 may retrieve 90 historic first systolic blood pressures of each patient from the training data set, calculate a statistical value of these 90 first systolic blood pressures, and then classify each patient into a plurality of patient clusters according to the aforementioned statistical value corresponding to each patient.

It is to be mentioned that in an embodiment of the disclosure, the classification factor may include mutual information. Namely, the processor 101 may calculate the mutual information of each patient according to the important feature variables of each patient. Then, the processor 101 may cluster the patients into the patient clusters by comparing the mutual information of each patient with the at least one cluster threshold. To be more detailed, the processor 101 may obtain the important feature variables of each patient within a previous month from the training data set to establish a plurality of probability distributions and calculate the mutual information of each patient according to the aforementioned probability distributions. The mutual information is a measure of mutual dependence between the variables, which may be obtained by Formula (1) below.

$$I(X; Y) = \sum_{y \in Y} \sum_{x \in X} p(x, y) \log\left(\frac{p(x, y)}{p(x)p(y)}\right),\quad \text{Formula (1)}$$

wherein p(x,y) is a joint probability distribution function of a variable X and a variable Y, p(x) is a marginal probability distribution of the variable X, and p(y) is a marginal probability distribution of the variable Y. In this case, the variable X and the variable Y are respectively the important feature variables of the embodiments of the disclosure. The variable X may be an important feature variable of a patient in a hemodialysis record one and a half months ago, for example, a previous systolic blood pressure, an average of two previous blood pressures, a first systolic blood pressure, a previous total ultrafiltration amount, a previous diastolic blood pressure, etc. The variable Y may be an important feature variable of another patient in the hemodialysis record one and a half months ago. Thereafter, the processor 101 may cluster the patients into 3, 4 or 5 patient clusters according to the value of the mutual information of each patient. The number of the patient clusters is not limited in the disclosure.

Figure 7:
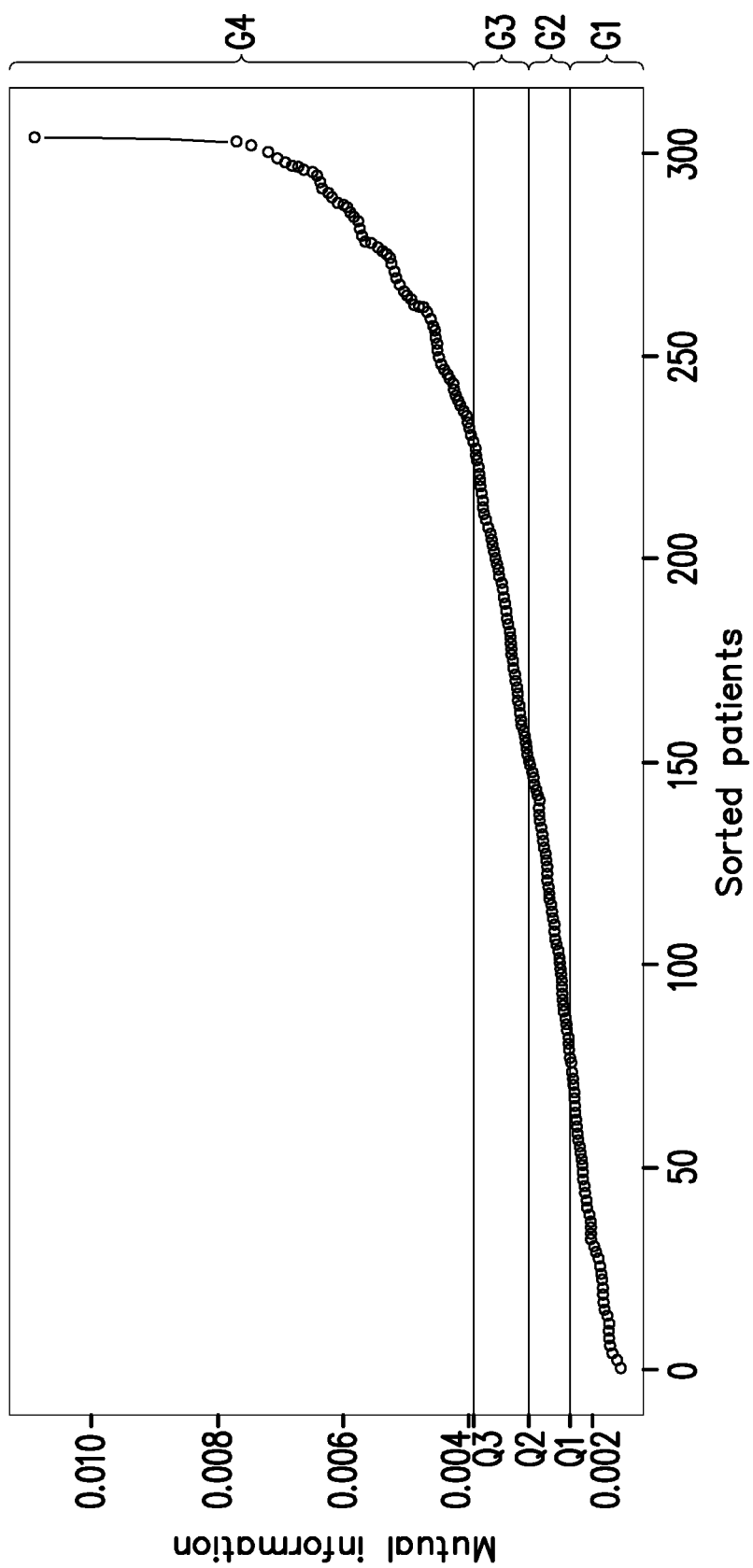
FIG. 7 is a schematic diagram illustrating patient classification according to an embodiment of the disclosure.

FIG. 7 is a schematic diagram illustrating patient classification according to an embodiment of the disclosure. Referring to FIG. 7, it is assumed that 300 patients are classified into 4 patient clusters according to the mutual information of each patient. In the example illustrated in FIG. 7, the classification thresholds are respectively equal to Q1, Q2 and Q3. Thus, the patients with the mutual information less than or equal to Q1 are clustered into a patient cluster G1, the patients with the mutual information greater than Q1 but less than or equal to Q2 are clustered into a patient cluster G2, the patients with the mutual information greater than Q2 but less than or equal to Q3 are clustered into a patient cluster G3, and the patients with the mutual information greater than Q3 are clustered into a patient cluster G4. In other words, the patients with blood pressure expressions that are close to one another during the period of hemodialysis are classified into the same patient cluster. The actual sizes and the number of the classification thresholds may be set based on actual demands.

In step S604, for each patient cluster, the processor 101 respectively trains a plurality of sub training data sets respectively corresponding to the patient clusters in the training data set according to a machine learning algorithm, so as to generate a plurality of second blood pressure prediction models respectively corresponding to the patient clusters. To be detailed, in response to the patients being classified into the patient clusters, the training data set of all the patients is also classified into a plurality of sub training data sets, such that the processor 101 may respectively train and obtain the plurality of second blood pressure prediction models according to the sub training data sets by using the machine learning algorithm. Accordingly, the second blood pressure prediction models correspond to the patient clusters one by one. Taking FIG. 7 for example, based on the patients being classified into the 4 patient clusters G1-G4, the processor 101 trains to obtain 4 second blood pressure prediction models according to the sub training data sets belonging to the 4 clusters of patients. The second blood pressure prediction models may be recorded in the storage circuit 102 and include first blood pressure prediction models. Because each patient has different body natures and clinical hemodialysis expressions, the processor 101 of the present embodiment may first classify the patients having similar body natures and clinical hemodialysis expressions into the same patient cluster and establish a blood pressure prediction model close to the actual clinical expression for each patient.

When the target patient checks in the medical institution, in step S605, the processor 101 determines the target patient as belonging to one of the patient clusters. Then, in step S606, the processor 101 selects the first blood pressure prediction model corresponding to one of the patient clusters from the second blood pressure prediction models. The first blood pressure prediction model is one of the second blood pressure prediction models. In other words, the processor 101 first determines the patient cluster of the target patient and obtains the corresponding first blood pressure prediction model from the second blood pressure prediction models to predict a blood pressure variation of the target patient during the period of hemodialysis. Accordingly, the patients belonging to different patient clusters use different first blood pressure prediction models for the prediction. With the corresponding blood pressure prediction model by classifying the patients, the blood pressure variation of the target patient may be predicted more preciously.

In step S607, the processor 101 receives the hemodialysis parameter data of the target patient, wherein the hemodialysis parameter data includes the first hemodialysis parameter at the previous time point and the second hemodialysis parameter at the current time point. In step S608, the processor 101 calculates the hemodialysis parameter variation amount between the first hemodialysis parameter and the second hemodialysis parameter. In step S609, the processor 101 provides the hemodialysis parameter variation amount to the first blood pressure prediction model to generate the prediction blood pressure variation associated with the next time point. In step S610, the processor 101 performs an operation according to the prediction blood pressure variation of the target patient. The operation of steps S607 through S610 is similar to that of steps S203 through S206 and thus, will not be repeated.

It should be mentioned that in an embodiment of the disclosure, since the target patient may have the specific first blood pressure prediction model according to the classification result thereof, a subsequent operation of generating the suggestion hemodialysis parameter value or an operation of simulating the simulation blood pressure variation according to the test hemodialysis parameter may also be performed according to the first blood pressure prediction model corresponding to the target patient. In this way, for a plurality of patients with physiological conditions that are dramatically different, the medical personnel may adaptively adjust the hemodialysis parameters of the dialysis apparatus according to different suggestion values and simulation values based on different blood pressure prediction models.

Figure 8:
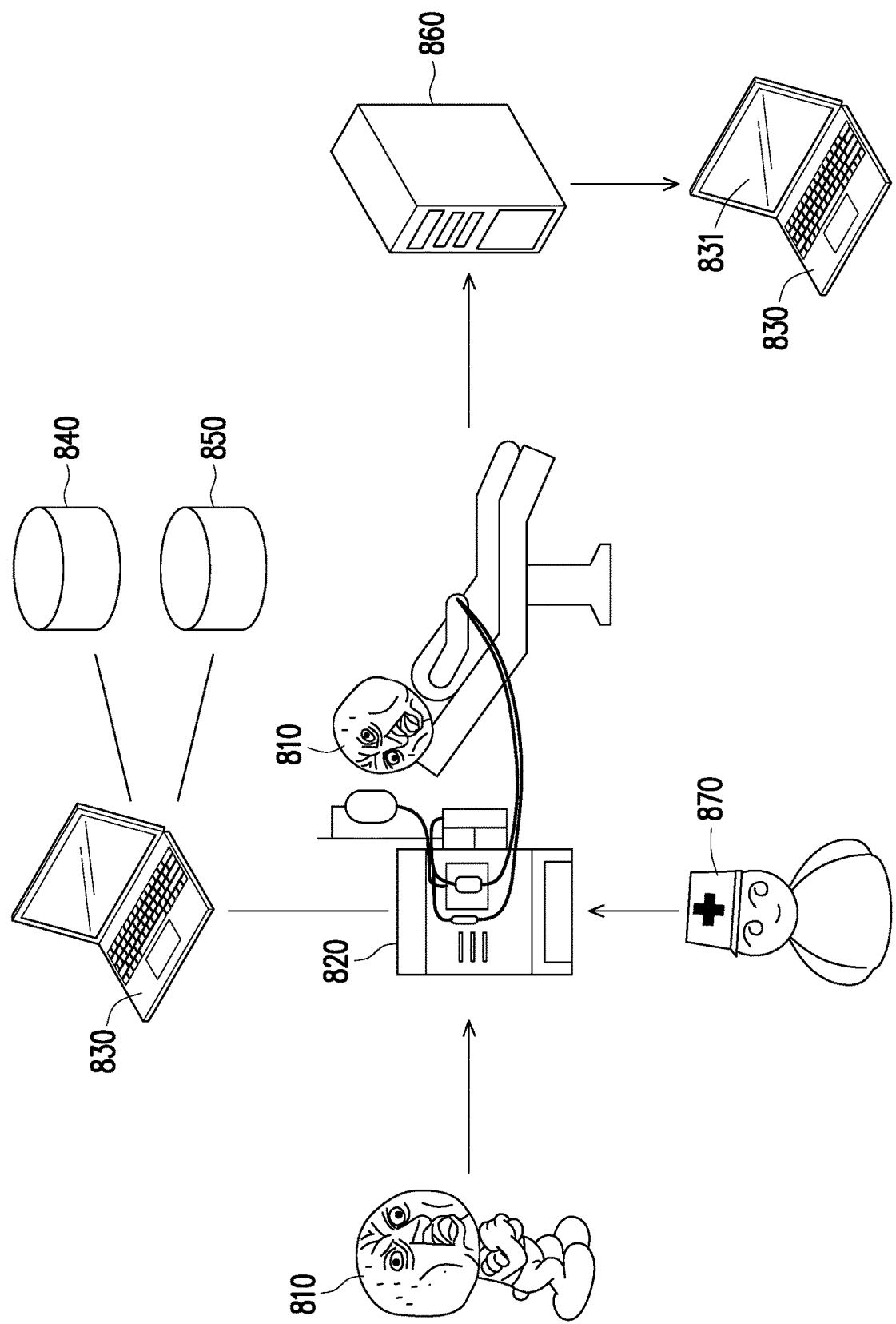
FIG. 8 illustrates an application scenario according to an embodiment of the disclosure.

FIG. 8 illustrates an application scenario according to an embodiment of the disclosure. Referring to FIG. 8, a target patient 810 checks in at the medical institution or the kidney dialysis center, and then, a medical personnel 870 assists to insert to a dialysis tube and configure a dialysis apparatus 820. Meanwhile, an on-site electronic apparatus 830 collects physiological data and hemodialysis therapy data of the target patient 810 input by the medical personnel 870. Moreover, the on-site electronic apparatus 830 may also receive the physiological data, medical record data and hemodialysis therapy data of the target patient 810 from a medical information system 840 through a network and may collect climate information from an external database 850. The on-site electronic apparatus 830 may also collect real-time hemodialysis parameter data from the dialysis apparatus 820.

Thereafter, the on-site electronic apparatus 830 uploads the collected physiological data, hemodialysis therapy data, climate data and medical record data to a cloud server 860. The cloud server 860 may perform data clearing, format arrangement, new variable generation and file string process, such as calculation of hemodialysis parameter variation amount. Then, the on-site electronic apparatus 830 may generate a prediction blood pressure variation result according to the organized data and the established blood pressure prediction model and prompt the prediction blood pressure variation result to a user interface 831. Accordingly, the medical personnel 870 may predict a blood pressure variation at each subsequent time point according to the user interface. Moreover, the medical personnel 870 may simulate the blood pressure variation of the target patient by inputting a test hemodialysis parameter through the user interface 831, thereby confirming whether stabilize the blood pressure of the patient may be stabilized by the adjusted hemodialysis parameter.

Based on the above, in the embodiments of the disclosure, the blood pressure variation during the period of hemodialysis may be predicted by the blood pressure prediction model established based on big data and the clinical data. Accordingly, the medical personnel can conduct treatments to the patient prior to the condition that the blood pressure is dropped to stabilize the blood pressure of the patient during the period of hemodialysis, thereby preventing discomfort or hemodialysis interruption form occurring to the patient. Furthermore, by automatically retrieving the physiological data and the hemodialysis therapy data of the patient and using the blood pressure prediction model for automated prediction, the burden of the medical personnel can be reduced, and further, inexperienced medical personnel can be provided with considerable assistance. In addition, by serving the hemodialysis parameter variation amount as input information of the blood pressure prediction model, a predication accuracy of the blood pressure variation may be improved based on more information amount. Moreover, the blood pressure variation can be estimated based on different blood pressure prediction models for different clusters of patients having obviously different clinical expressions for hemodialysis, so as to enhance the accuracy of the prediction blood pressure variation.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A blood pressure prediction method, adapted to an electronic apparatus comprising a processor and a storage circuit, comprising:
   collecting a training data set;
   establishing a first blood pressure prediction model according to the training data set;
   receiving hemodialysis parameter data of a target patient, wherein the hemodialysis parameter data comprises a first hemodialysis parameter at a previous time point and a second hemodialysis parameter at a current time point;
   calculating a hemodialysis parameter variation amount between the first hemodialysis parameter and the second hemodialysis parameter;
   providing the hemodialysis parameter variation amount to the first blood pressure prediction model to generate a prediction blood pressure variation associated with a next time point; and
   in response to the prediction blood pressure variation associated with the next time point being greater than an alert threshold, performing an operation according to the prediction blood pressure variation of the target patient, wherein the operation comprising:
   generating a suggestion hemodialysis parameter value according to the first blood pressure prediction model and the second hemodialysis parameter at the current time point through minimizing an output of the first blood pressure prediction model; and
   prompting the suggestion hemodialysis parameter value or set a dialysis apparatus according to the suggestion hemodialysis parameter value.

2. The blood pressure prediction method according to claim 1, further comprising:
   receiving physiological data and medical record data of the target patient and climate data; and
   providing the physiological data, the medical record data and the climate data to the first blood pressure prediction model to generate the prediction blood pressure variation associated with the next time point.

3. The blood pressure prediction method according to claim 1, wherein the first hemodialysis parameter and the second hemodialysis parameter comprise ultrafiltration rates, dialysate concentrations, dialysate temperatures or blood flow rates.

4. The blood pressure prediction method according to claim 1, further comprising:
   in response to the prediction blood pressure variation associated with the next time point being greater than the alert threshold, issuing an alarm notification.

5. The blood pressure prediction method according to claim 4, further comprising:
   receiving a test hemodialysis parameter;
   providing another hemodialysis parameter variation amount between the second hemodialysis parameter and the test hemodialysis parameter to the first blood pressure prediction model to generate a simulation blood pressure variation; and
   prompting the simulation blood pressure variation.

6. The blood pressure prediction method according to claim 1, wherein the step of establishing the first blood pressure prediction model according to the training data set comprises:
   acquiring a plurality of important feature variables from the training data set;
   generating a classification factor of each patient according to the important feature variables of each patient, and classifying the patients into a plurality of patient clusters according to the classification factor of each patient; and
   for each of the patient clusters, respectively training a plurality of sub training data sets respectively corresponding to the patient clusters in the training data set according to a machine learning algorithm to generate a plurality of second blood pressure prediction models respectively corresponding to the patient clusters, wherein the second blood pressure prediction models comprise the first blood pressure prediction model.

7. The blood pressure prediction method according to claim 6, further comprising:
   determining the target patient as belonging to one of the patient clusters; and
   selecting the first blood pressure prediction model corresponding to the one of the patient clusters from the second blood pressure prediction models.

8. The blood pressure prediction method according to claim 6, wherein the step of generating the classification factor of each patient according to the important feature variables of each patient and classifying the patients into the patient cluster according to the classification factor of each patient comprises:

calculating mutual information of each patient according to the important feature variables of each patient; and
 clustering the patients into the patient clusters by comparing the mutual information of each patient with at least one cluster threshold.

9. The blood pressure prediction method according to claim 6, wherein the machine learning algorithm is a supervised machine learning algorithm.

10. An electronic device, comprising:
 a storage circuit, storing a plurality of modules; and
 a processor, coupled to the storage circuit and configured to access the modules to:
  collect a training data set;
  establish a first blood pressure prediction model according to the training data set;
  receive hemodialysis parameter data of a target patient, wherein the hemodialysis parameter data comprises a first hemodialysis parameter at a previous time point and a second hemodialysis parameter at a current time point;
  calculate a hemodialysis parameter variation amount between the first hemodialysis parameter and the second hemodialysis parameter;
  provide the hemodialysis parameter variation amount to the first blood pressure prediction model to generate a prediction blood pressure variation associated with a next time point; and
  in response to the prediction blood pressure variation associated with the next time point being greater than an alert threshold, perform an operation according to the prediction blood pressure variation of the target patient, wherein the operation comprising:
   generating a suggestion hemodialysis parameter value according to the first blood pressure prediction model and the second hemodialysis parameter at the current time point through minimizing an output of the first blood pressure prediction model; and
   prompting the suggestion hemodialysis parameter value or set a dialysis apparatus according to the suggestion hemodialysis parameter value.

11. The electronic device according to claim 10, wherein the processor is configured to:
 receive physiological data and medical record data of the target patient and climate data; and
 provide the physiological data, the medical record data and the climate data to the first blood pressure prediction model to generate the prediction blood pressure variation associated with the next time point.

12. The electronic device according to claim 10, wherein the first hemodialysis parameter and the second hemodialysis parameter comprise ultrafiltration rates, dialysate concentrations, dialysate temperatures or blood flow rates.

13. The electronic device according to claim 10, wherein the processor is configured to:
 in response to the prediction blood pressure variation associated with the next time point being greater than the alert threshold, issue an alarm notification.

14. The electronic device according to claim 13, wherein the processor is configured to:
 receive a test hemodialysis parameter;
 provide another hemodialysis parameter variation amount between the second hemodialysis parameter and the test hemodialysis parameter to the first blood pressure prediction model to generate a simulation blood pressure variation; and
 prompt the simulation blood pressure variation.

15. The electronic device according to claim 10, wherein the processor is configured to:
 acquire a plurality of important feature variables from the training data set;
 generate a classification factor of each patient according to the important feature variables of each patient, and classify the patients into a plurality of patient clusters according to the classification factor of each patient; and
 for each of the patient clusters, respectively train a plurality of sub training data sets respectively corresponding to the patient clusters in the training data set according to a machine learning algorithm to generate a plurality of second blood pressure prediction models respectively corresponding to the patient clusters, wherein the second blood pressure prediction models comprise the first blood pressure prediction model.

16. The electronic device according to claim 15, wherein the processor is configured to:
 determine the target patient as belonging to one of the patient clusters; and
 select the first blood pressure prediction model corresponding to the one of the patient clusters from the second blood pressure prediction models.

17. The electronic device according to claim 15, wherein the processor is configured to:
 calculate mutual information of each patient according to the important feature variables of each patient; and
 cluster the patients into the patient clusters by comparing the mutual information of each patient with at least one cluster threshold.

18. The electronic device according to claim 15, wherein the machine learning algorithm is a supervised machine learning algorithm.

\* \* \* \* \*